(12) United States Patent
Mikkaichi et al.

(10) Patent No.: US 8,647,353 B2
(45) Date of Patent: Feb. 11, 2014

(54) ENDOSCOPIC TREATMENT TOOL AND SUTURING METHOD USING THE SAME

(75) Inventors: Takayasu Mikkaichi, Tokyo (JP); Kunihide Kaji, Tokyo (JP); Junichi Kobayashi, Fujinomiya (JP); Takayuki Suzuki, Yokohama (JP); Takahiro Kogasaka, Tokyo (JP); Yasushi Kinoshita, Fujinomiya (JP); Tadashi Kousai, Fujinomiya (JP)

(73) Assignees: Olympus Medical Systems Corp., Tokyo (JP); Kaisha, Terumo Kabushiki, Tokyo (JP)

(*) Notice: Subject to any disclaimer, the term of this patent is extended or adjusted under 35 U.S.C. 154(b) by 1155 days.

(21) Appl. No.: 11/965,299

(22) Filed: Dec. 27, 2007

(65) Prior Publication Data

US 2008/0242933 A1    Oct. 2, 2008

Related U.S. Application Data

(60) Provisional application No. 60/877,701, filed on Dec. 28, 2006.

(51) Int. Cl.
*A61B 17/10* (2006.01)
*A61B 17/08* (2006.01)

(52) U.S. Cl.
USPC ............................ 606/142; 606/153; 606/139

(58) Field of Classification Search
USPC ......... 606/139, 144–146, 142, 143, 148, 153, 606/213, 215, 216; 227/175.1; 600/128, 600/158, 104
See application file for complete search history.

(56) References Cited

U.S. PATENT DOCUMENTS

| | | | | |
|---|---|---|---|---|
| 5,374,275 A | * | 12/1994 | Bradley et al. | 606/144 |
| 5,397,325 A | * | 3/1995 | Della Badia et al. | 606/144 |
| 5,403,329 A | * | 4/1995 | Hinchcliffe | 606/147 |
| 5,454,823 A | * | 10/1995 | Richardson et al. | 606/148 |
| 5,503,634 A | * | 4/1996 | Christy | 606/144 |
| 5,507,755 A | * | 4/1996 | Gresl et al. | 606/139 |
| 5,562,686 A | * | 10/1996 | Sauer et al. | 606/144 |
| 5,613,975 A | * | 3/1997 | Christy | 606/144 |

(Continued)

FOREIGN PATENT DOCUMENTS

| | | |
|---|---|---|
| JP | 2005-512667 A | 5/2005 |
| WO | WO 03/053253 A1 | 7/2003 |

(Continued)

OTHER PUBLICATIONS

Japanese Office Action dated May 22, 2012 from corresponding Japanese Patent Application No. 2007-334560.

*Primary Examiner* — Corrine M McDermott
*Assistant Examiner* — Christopher L Templeton
(74) *Attorney, Agent, or Firm* — Scully, Scott, Murphy & Presser, P.C.

(57) ABSTRACT

An endoscopic treatment tool according to the present invention is an endoscopic treatment tool which is inserted into hollow organs via the mouth, nose, anus, or other natural orifice of the patient and performs suturing treatment within the hollow organs or abdominal cavities, includes: a hollow organ lining support which is smaller than the smallest diameter of a passage from a natural orifice of the hollow organ, the hollow organ lining support being able to expand so as to have a diameter larger than the smallest diameter of the passage from the natural orifice of the hollow organ.

3 Claims, 14 Drawing Sheets

(56) References Cited

U.S. PATENT DOCUMENTS

| | | | |
|---|---|---|---|
| 5,707,379 A * | 1/1998 | Fleenor et al. | 606/145 |
| 5,836,955 A * | 11/1998 | Buelna et al. | 606/148 |
| 5,868,762 A * | 2/1999 | Cragg et al. | 606/144 |
| 6,074,401 A * | 6/2000 | Gardiner et al. | 606/139 |
| 6,558,400 B2 * | 5/2003 | Deem et al. | 606/151 |
| 6,702,825 B2 * | 3/2004 | Frazier et al. | 606/139 |
| 6,767,352 B2 * | 7/2004 | Field et al. | 606/148 |
| 7,059,331 B2 * | 6/2006 | Adams et al. | 128/898 |
| 7,083,630 B2 * | 8/2006 | DeVries et al. | 606/153 |
| 7,377,926 B2 * | 5/2008 | Topper et al. | 606/144 |
| 7,462,188 B2 * | 12/2008 | McIntosh | 606/213 |
| 7,553,317 B2 * | 6/2009 | Weisenburgh et al. | 606/153 |
| 7,559,938 B2 * | 7/2009 | Hess et al. | 606/153 |
| 7,666,195 B2 * | 2/2010 | Kelleher et al. | 606/144 |
| 7,758,597 B1 * | 7/2010 | Tran et al. | 606/144 |
| 7,815,659 B2 * | 10/2010 | Conlon et al. | 606/198 |
| 7,842,048 B2 * | 11/2010 | Ma | 606/144 |
| 7,842,049 B2 * | 11/2010 | Voss | 606/144 |
| 7,850,701 B2 * | 12/2010 | Modesitt et al. | 606/144 |
| 8,252,009 B2 * | 8/2012 | Weller et al. | 606/151 |
| 2001/0031973 A1 * | 10/2001 | Nobles et al. | 606/144 |
| 2003/0065359 A1 | 4/2003 | Weller et al. | |
| 2003/0109892 A1 | 6/2003 | Deem et al. | |
| 2003/0127491 A1 | 7/2003 | Adams et al. | |
| 2004/0024386 A1 | 2/2004 | Deem et al. | |
| 2004/0193190 A1 * | 9/2004 | Liddicoat et al. | 606/153 |
| 2004/0236357 A1 * | 11/2004 | Kraemer et al. | 606/151 |
| 2005/0288690 A1 * | 12/2005 | Bourque et al. | 606/144 |
| 2006/0253127 A1 | 11/2006 | Bjerken | |
| 2007/0203507 A1 * | 8/2007 | McLaughlin et al. | 606/144 |
| 2007/0255100 A1 * | 11/2007 | Barlow et al. | 600/114 |

FOREIGN PATENT DOCUMENTS

| | | |
|---|---|---|
| WO | WO 2004/004542 A2 | 1/2004 |
| WO | WO 2004/050971 A2 | 6/2004 |
| WO | WO 2005/034729 A2 | 4/2005 |
| WO | WO 2006/023764 A2 | 3/2006 |
| WO | WO 2006/112849 A1 | 10/2006 |

\* cited by examiner

ENDOSCOPIC TREATMENT TOOL AND SUTURING METHOD USING THE SAME

BACKGROUND OF THE INVENTION

1. Field of Invention

The present invention relates to an endoscopic treatment tool and suturing method using the same.

2. Description of Related Art

In recent years, methods of performing procedures on hollow organs such as stomach via the mouth, nose, anus, or other natural orifice of the patient by inserting a flexible endoscope along with such as suturing tools to suture the hollow organs into a tubular shape have been known as methods of reducing the burden on the patient.

Examples of such procedures are disclosed in W.O. Patent Application No. 2004/050971, U.S. Patent Application No. 2003/0065359, U.S. Patent Application No. 2004/0024386, U.S. Patent Application No. 2003/0109892.

SUMMARY OF THE INVENTION

An object of this invention is to provide an endoscopic treatment tool and suturing methods using the same, that can suture the inside wall of hollow organs into a tubular shape with desirable diameters via a natural orifice.

An endoscopic treatment tool according to a first aspect of this invention is an endoscopic treatment tool which is inserted into a hollow organ via a natural orifice and performs a suturing procedure within the hollow organ or abdominal cavities, includes a hollow organ lining support which is smaller than the smallest diameter of a passage from the natural orifice to the hollow organ, a portion of the hollow organ lining support being able to expand so as to have a diameter larger than the smallest diameter of the passage from the natural orifice to the hollow organ.

A high-frequency treatment tool according to a second embodiment of the present invention is a high-frequency treatment tool which is inserted into a hollow organ via a natural orifice, and performs a suturing procedure within the hollow organs or abdominal cavities, includes a high-frequency electrode which is inserted into an instrument channel of the endoscope so as to freely protrude and retract, and high-frequency electricity is applied.

Furthermore, a high-frequency treatment tool according to a third embodiment of the present invention is a high-frequency treatment tool which is inserted into a hollow organ via a natural orifice and perform a suturing procedure within the hollow organ or abdominal cavities, includes a cap which is detachably disposed at a distal end of an endoscope, and a high-frequency electrode in which a high-frequency electricity is applied thereto is disposed on the cap.

Furthermore, a suturing method according to a fourth embodiment of the present invention is a suturing method using a high-frequency treatment tool which is inserted into a hollow organ via a natural orifice and performs a suturing procedure of suturing the hollow organ lining, including the steps of; inserting a hollow organ lining support provided on the endoscopic treatment tool, which is smaller than the smallest diameter of a passage from the natural orifice to the hollow organ, a portion of the hollow organ lining support being able to expand so as to have a diameter larger than the smallest diameter of the passage from the natural orifice to the hollow organ; expanding at least a portion of the hollow organ lining support within the hollow organ; and suturing the hollow organ lining into a tubular shape.

DETAILED DESCRIPTION OF THE INVENTION

Embodiments according to the present invention will be described in detail below. In the following description, components that are the same shall be provided with the same reference symbols and redundant descriptions will be omitted.

A First Embodiment

Figure 1:
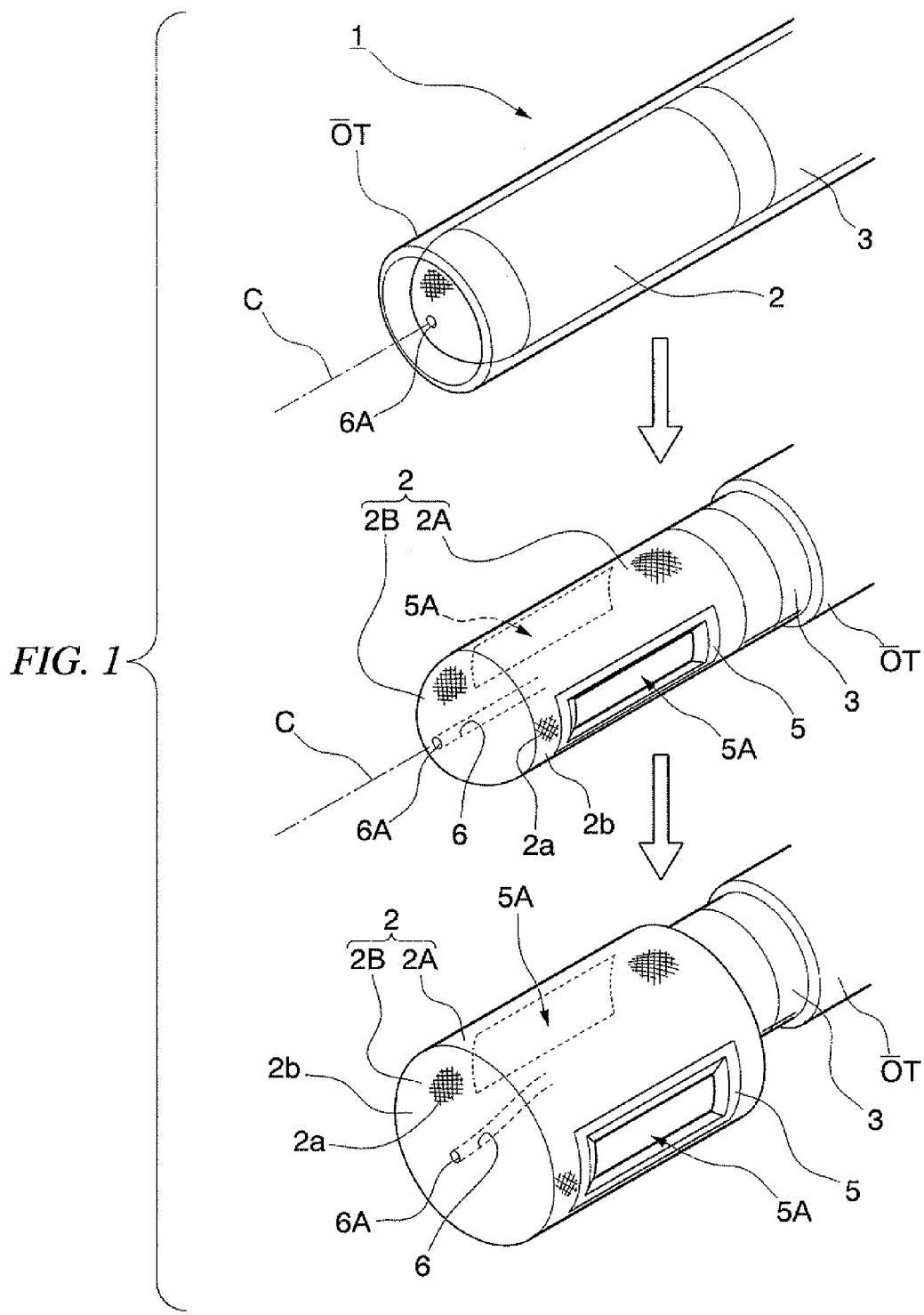
FIG. 1 is a diagram showing the principal portions of the suturing tool according to a first embodiment.
Figure 2:
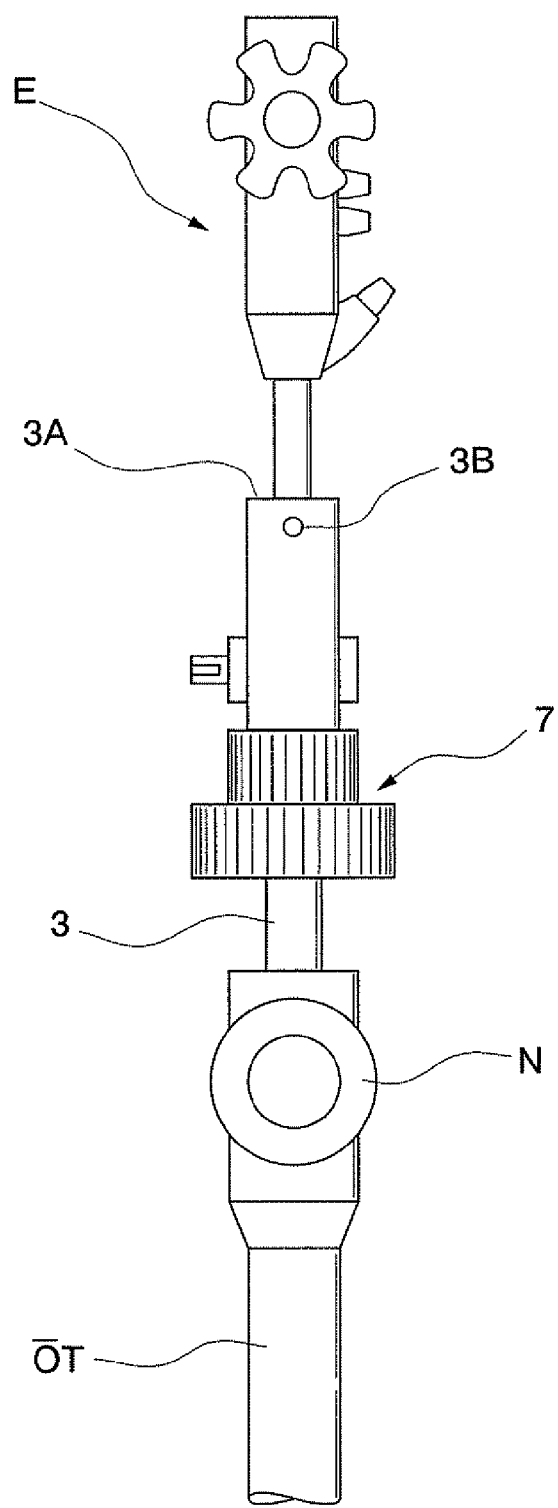
FIG. 2 is a diagram showing a proximal side of the suturing tool according to the first embodiment.

As shown in FIGS. 1 and 2, a suturing tool as an endoscopic treatment tool 1 according to the present invention is a suturing tool which is inserted into a stomach (hollow organ) via the mouth, nose, anus or other natural orifice, and performs a suturing treatment inside of the stomach or abdominal cavity.

The suturing tool 1 includes a hollow organ lining support 2 (herein after abbreviated as a stomach wall support) which is smaller than the smallest diameter of a passage from the natural orifice to the hollow organ, a portion of the hollow organ lining support being able to expand so as to have a diameter larger than the smallest diameter of a diameter of cardia of stomach, in other words, the passage from the natural orifice to the hollow organ; and an inner tube 3 which connects to a tubular body 2A which is described later, of the stomach wall support 2.

The stomach wall support 2 includes the tubular body 2A including fine threads 2a netted into a cylindrical shape and a lateral face thereof is covered with a film 2b, and a distal end portion 2B consisted of fine threads 2a netted to cover the distal end open portion of the tubular body 2A and is also covered with the film 2b.

A pair of plates 5A provided with a window (open portion) 5A thereon are disposed on the lateral face of the tubular body 2A symmetrically with respect to the central axis C. The number of window 5A is not limited thereto. One or a plurality of windows may be provided.

A proximal end of the tubular body 2A is connected to the inner tube 3. The tubular body 2A accommodates a suturing needle not illustrated. The tubular body 2A also includes an aspiration lumen 6 connected to an aspirator (not illustrated).

The 2B is disposed to cover the distal opening of the tubular body 2A, and an opening 6A of the aspiration lumen 6 is disposed on a center thereof. Upon compression of the tubular body 2A, the distal end portion 2B is compressed such that the center is projected out to the distal end. Upon dilation of the tubular body 2A, the distal end portion 2B is dilated so as to deform into a plane.

The stomach wall support 2 is inserted into the overtube OT in which the outer diameter has a substantially same diameter as an inner diameter of the cardia CA, in a compressed state. The distal end of the overtube OT generates various curved movements with an operation of a curved knob N disposed at a proximal end of the overtube OT.

An outer diameter of the inner tube 3 has a diameter substantially equal to an outer diameter of the compressed state of the tubular body 2A. An operation knob 7 which operates a suturing needle (a suturing tool) housed in the tubular body 2A is provided at the proximal end thereof. An insertion opening 3A of the endoscope E is provided at a distal end of the inner tube 3. An aspiration opening 3B which is connected to a distal end of the aspiration lumen 6 is disposed in the vicinity of the insertion opening 3A.

Figure 3:
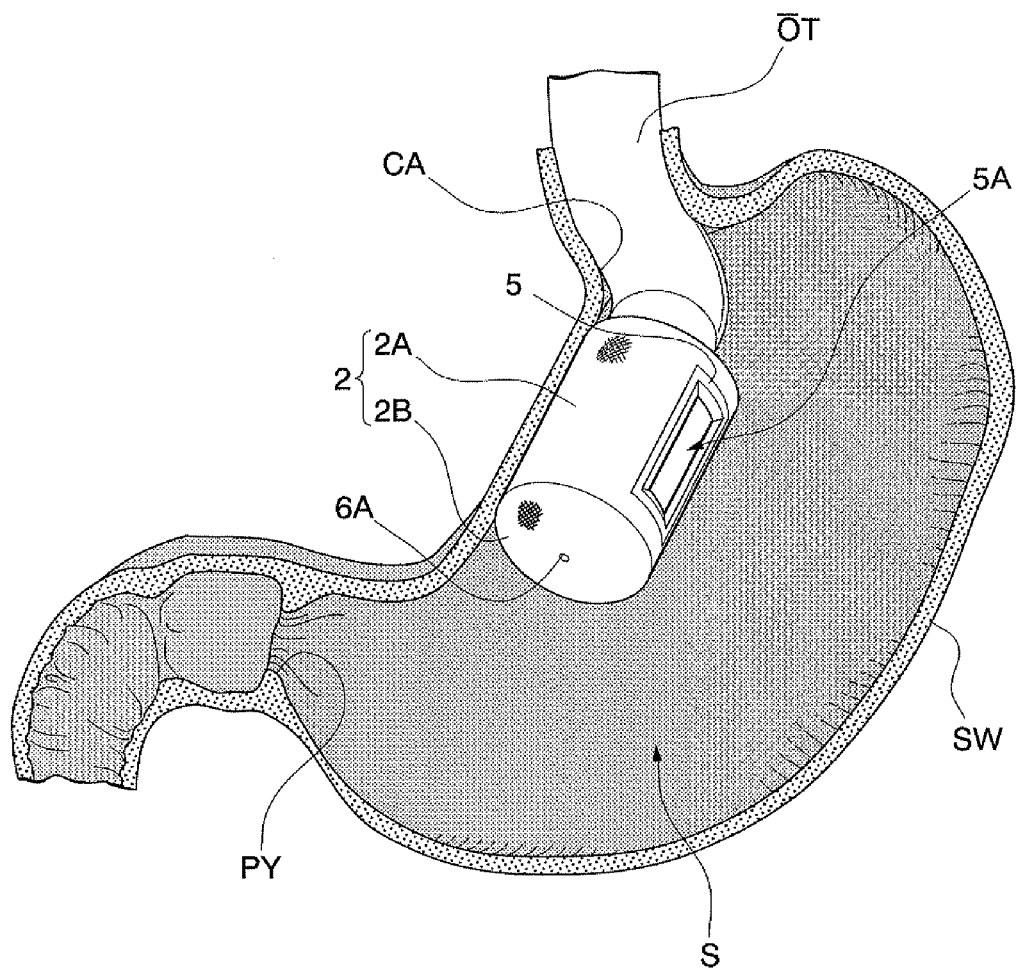
FIG. 3 is a diagram for showing a state of the expanding suturing tool inside of the stomach in the suturing procedure according to the first embodiment.
Figure 4:
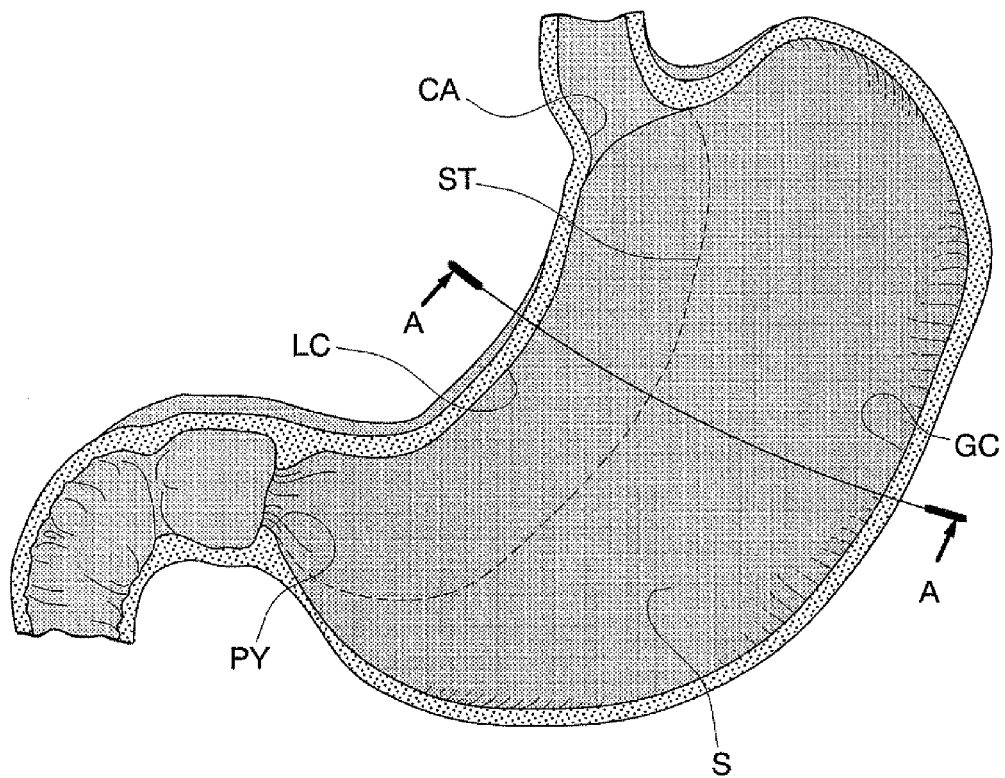
FIG. 4 is a diagram for showing a state of suturing the stomach wall in the suturing procedure according to the first embodiment.
Figure 5:
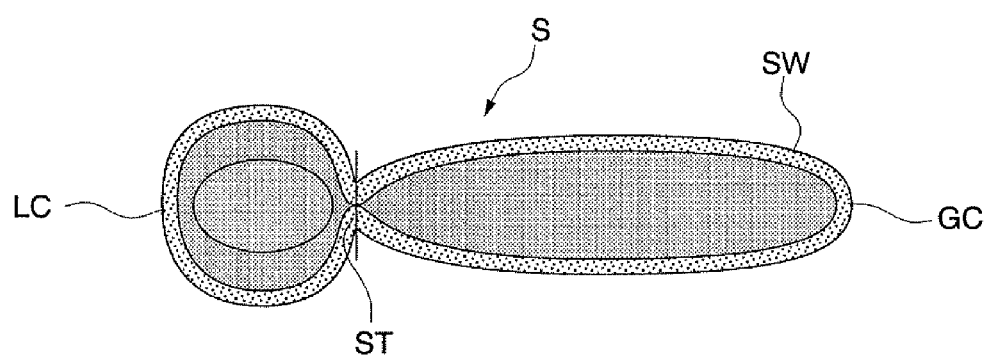
FIG. 5 is a cross-sectional view as seen from the line A-A in FIG. 4.

The actions of the present embodiment will now be described in line with a suturing procedure as shown by FIG. 3 to 5.

The suturing procedure according to the present embodiment consists of an insertion step (S01) of inserting the overtube OT containing the stomach wall support 2, into the stomach S via the mouth of the patient; a distending step (S20) in which the diameter of the stomach wall support 2 is expanded within the stomach S; and a suturing step (S03) of suturing a stomach wall SW from the cardia CA to a pylorus PY into a tubular shape.

First, the insertion step (S01) is performed by inserting the overtube OT accommodating the stomach wall support 2 and the inner tube 3 therein, into in the vicinity of the cardia CA of the stomach S via the mouth of the patient. At this time, the stomach wall support 2 is in a compressed status into an inner radial direction pressed by the overtube OT.

Next, the distending step is performed by shifting the overtube OT to a proximal side relative to the inner tube 3 so as to expose the stomach wall support 2. From this movement, the stomach wall support 2 is released from the OT compressing the lateral face of the stomach wall support 2 into the radial direction, and the diameter of the stomach wall support 2 expands to its original outer diameter size which is larger than the diameter of the cardia CA as shown in FIG. 3. At this time, the distal end portion 2B is also deformed into a flat plane after expansion of the diameter.

Then the suturing step (S03) is performed by aspirating the stomach S by the aspiration lumen 6 accompanying the unshown aspirator, and the stomach S is contracted. Upon contraction of the stomach S, the stomach wall SW attaches onto the stomach wall support 2. By further reducing the internal pressure of the stomach wall support 2 compared to the pressure of the stomach S, a part of the stomach wall SW is pulled into the windows 5A so as to aspirate the stomach wall SW, resulting the formation of a tubular section having a diameter larger than the inner diameter of the cardia CA within the stomach S by the stomach wall support 2.

The stomach wall SW pulled into the windows 5A is later sutured by the suturing needle not illustrated. Suturing is performed by moving the inner tube 3 or by moving the overtube OT in conjunction with the movement of the inner tube 3 accompanying the overtube OT, so that stitches ST are lined up along a lesser curvature LC from the cardia CA to the pylorus PY of the stomach S as shown in FIG. 4.

Figure 6:
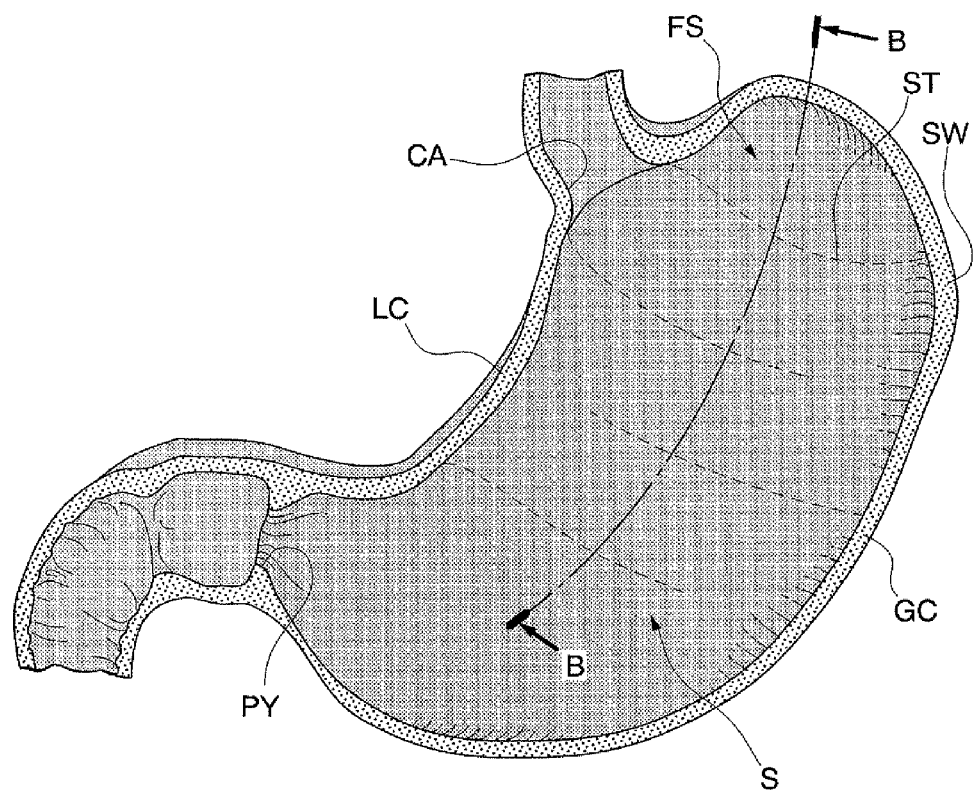
FIG. 6 is a diagram for showing a state of suturing the stomach wall in the modified suturing procedure according to the first embodiment.
Figure 7:
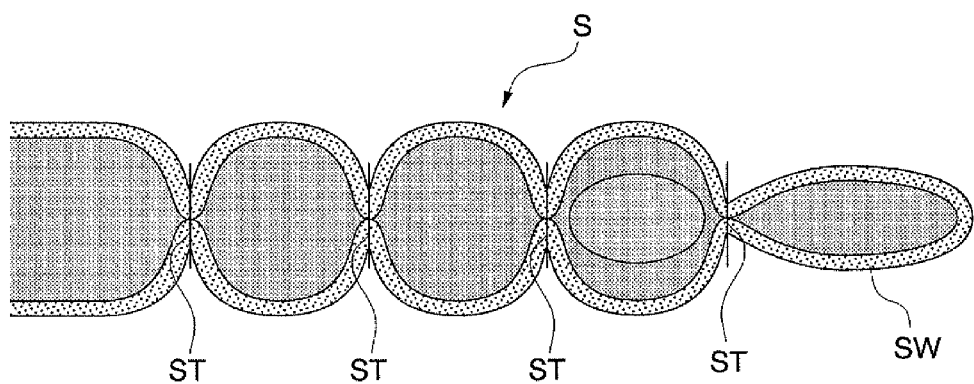
FIG. 7 is a cross-sectional view as seen from the line B-B in FIG. 6.
Figure 8:
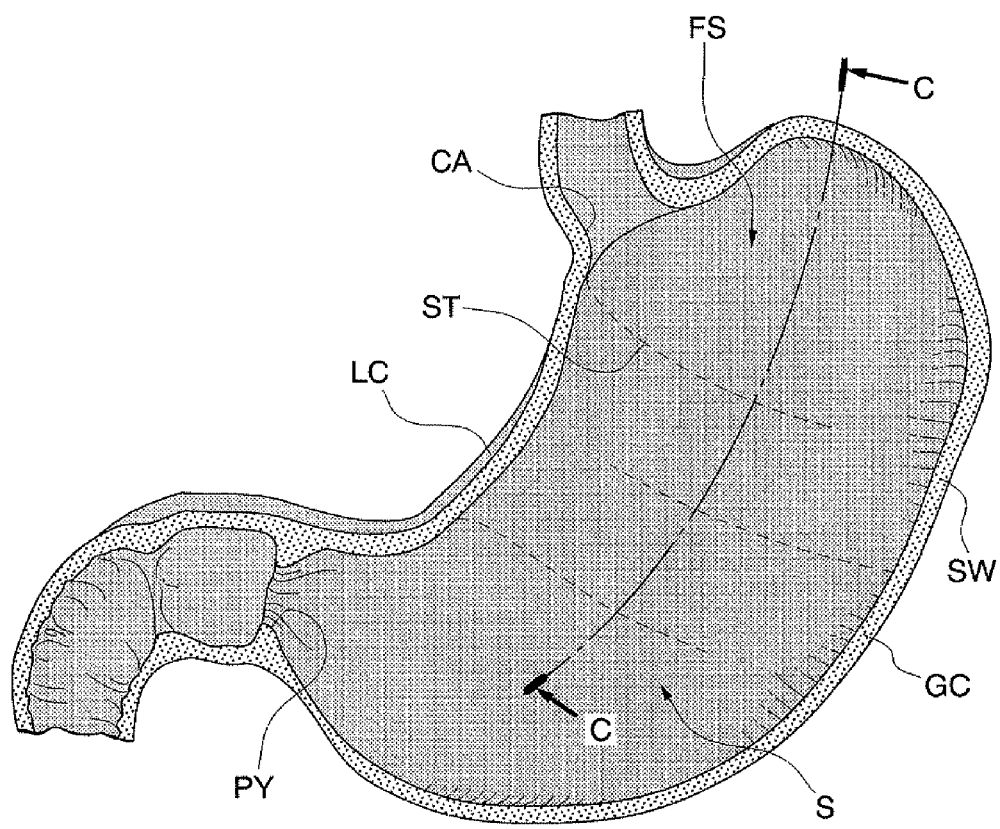
FIG. 8 is a diagram for showing a state of suturing the stomach wall in the modified suturing procedure according to the first embodiment.
Figure 9:
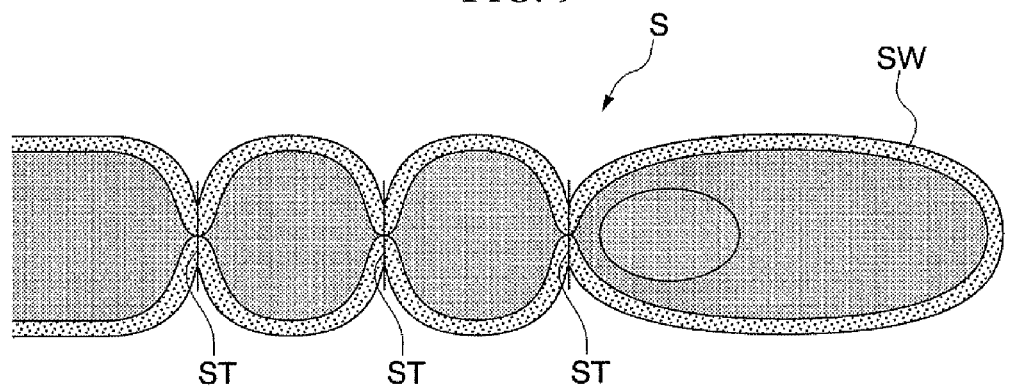
FIG. 9 is a cross-sectional view as seen from the line C-C in FIG. 8.
Figure 10:
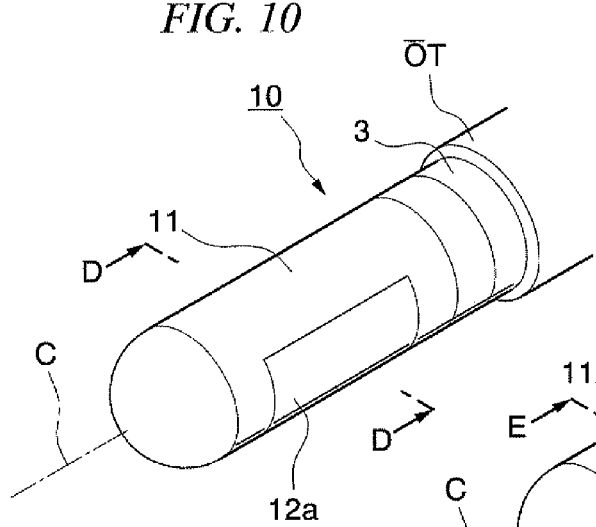
FIG. 10 is a diagram showing the principal portions of the suturing tool according to a second embodiment.
Figure 12:
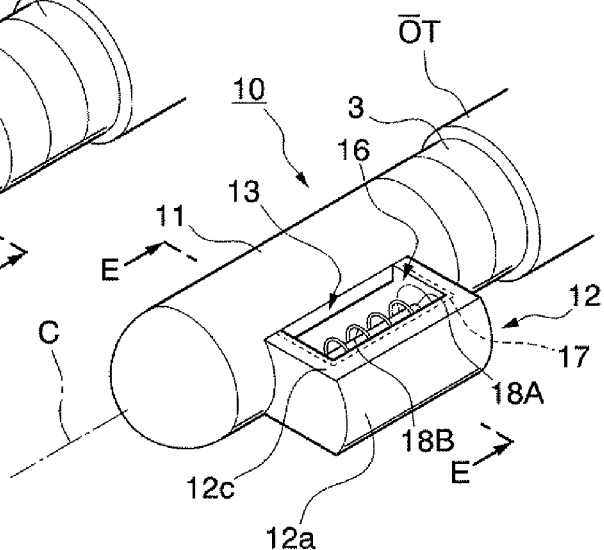
FIG. 12 is a diagram showing the principal portions of a suturing tool according to the second embodiment.
Figure 11:
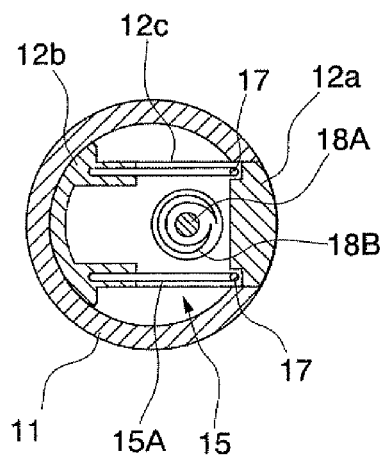
FIG. 11 is a cross-sectional view as seen from the line D-D in FIG. 10.
Figure 13:
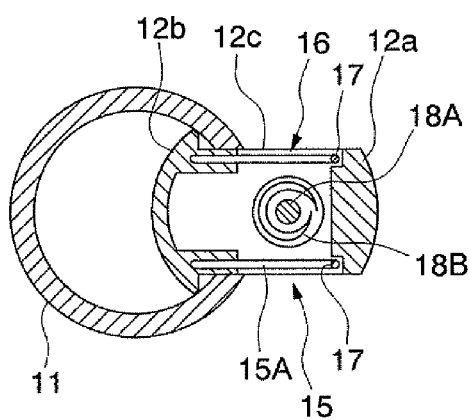
FIG. 13 is a cross-sectional view as seen from the line E-E in FIG. 12.
Figure 14:
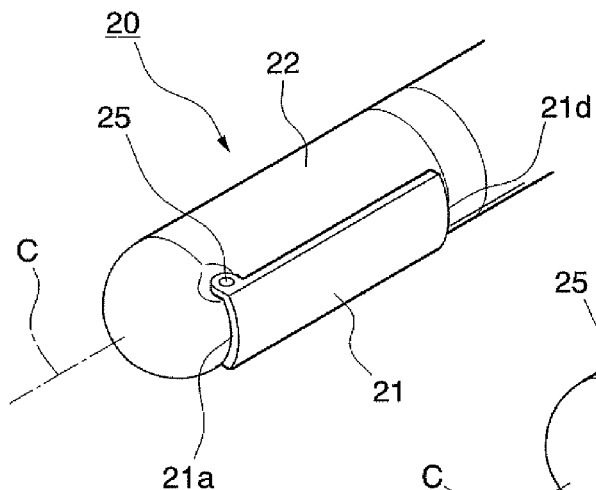
FIG. 14 is a diagram showing the principal portions of a suturing tool according to a third embodiment.
Figure 15:
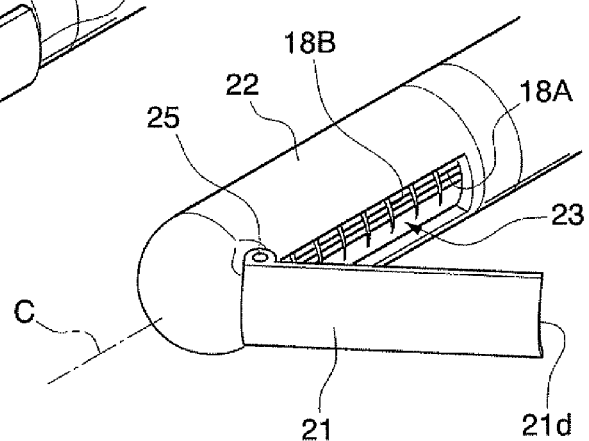
FIG. 15 is a diagram showing the principal portions of the suturing tool according to the third embodiment.

Alternatively, as shown in FIGS. 6 and 7, suturing from the cardia CA to the pylorus PY may be performed by; suturing in a straight line from the lesser curvature LC to the vicinity of a greater curvature GC of the stomach (but not suturing all the way to the CC); then suturing in a straight line from the greater curvature GC to the vicinity of the lesser curvature LC (but not suturing all the way to the lesser curvature LC) from the pylorus PY side at a predetermined distance away. This suturing method may be repeated in sequence a plurality of times so that stitches reach the vicinity of the pylorus PY. In this case, suturing may be performed so as to clinch a fundus of stomach FS as shown in FIGS. 6 and 7, or without such clinching as shown in FIGS. 8 and 9.

After suturing is completed, the inner tube 3 is moved with respect to the overtube OT, so that the stomach wall support 2 is received by being compressed into the overtube OT. Once the stomach wall support 2 is completely received inside of the overtube OT, the entire suturing tool 1 and the overtube OT are drawn out from the mouth of the patient.

According to the suturing tool 1 and the suturing methods using the same, the tubular section in which the inner diameter is larger than the inner diameter of the cardia CA can be formed within the stomach S by virtue of a provision of the stomach wall support 2 then sutured into the tubular section by expansion of the stomach wall support 2 within the stomach S. Because the windows 5A are disposed on the stomach wall support 2, suturing with the unshown suturing needle can be performed via the windows 5A. Furthermore, the stomach wall support 2 is provided with the overtube OT which freely advances and retracts with respect to the stomach wall support 2, thereby the size of the stomach wall support 2 can be adjusted according to a protrusion or recession amount of the stomach wall support 2 from the overtube OT.

Second Embodiment

Next, a second embodiment will be described in line with FIGS. 10 to 13.

The second embodiment differs from the first embodiment in that a tubular body 11 of a suturing tool 10 in the present embodiment is a rigid body being able to pass through the cardia CA of the stomach S, and a stomach wall support 12 is disposed as a part of a lateral face of the tubular body 11, so as to protrude and retract with respect to the tubular body 11.

An opening portion 13 is provided on the lateral face of the tubular body 11 for the stomach wall support 12 being able to protrude and retract with respect to the tubular body 11.

A suturing tool 10 includes a transfer mechanism 15 which makes the stomach wall support 12 protrude and retract with respect to the opening portion 13 in a radial direction (normal line direction to the opening portion 13). The transfer mechanism 15 is the rigid body and includes an operation wire 15A in which the distal end is fixed to the tubular body 11. A proximal end of the operation wire 15A extends to an operation section proximal to an operator. A proximal end of the tubular body 11 is connected to the inner tube 3.

The stomach wall support 12 is surrounded by an outer lateral face 12a, an inner lateral face 12b, and a pair of aspiration faces 12c; the outer lateral face 12a which is a part of the lateral face of the tubular body 11, the inner lateral face 12b which comes into contact with an inner lateral face of the tubular body 11 which is symmetrical to the opening portion 13 and a pair of aspiration faces 12c in which a pair of windows 16 where stomach wall SW is aspirated into are provided on both aspiration faces 12c.

A pair of high-frequency electrodes 17 is provided on an inner side of the outer lateral face 12a in order to cauterize the stomach wall SW aspirated from the windows 16.

The high-frequency electrodes 17 are connected to an operation section proximal to the operator not illustrated via the operation wire 15A, the high-frequency electrodes 17 are moved to the tubular body 11 side by crossing through the window 16 upon pulling the operation wire 115A by the operation of the operation section.

The inner lateral face 12b is in arc-shape formed along the shape of the inner lateral face of the tubular body 11. Since the surface area of the arc-shape of the inner lateral face 12b is larger than the opened area of the opening portion 13, the inner lateral face 12b is detained inside of the tubular body 11.

The pair of windows 16 are disposed so as to oppose each other, in a direction perpendicular to the central axis C. An axis 18A which is connected to an operation knob is provided in the stomach wall support 12 along the inner lateral face 12b and the outer lateral face 12a of the stomach wall support 12. Furthermore, a plurality of ring-shaped suturing needles 18B are disposed with a predetermined distance apart from each other around the axis 18A as the center of the needles 18B.

The actions of the present embodiment will now be described in line with the suturing tool 10

The suturing procedure according to the present embodiment consists of an insertion step (S11) of inserting the overtube OT provided with the stomach wall support 12 into the stomach S via the mouth of the patient; a distending step (S12) in which the stomach wall support 12 is projected out from the tubular body 11 within the stomach S; and a suturing step (S13) of suturing the stomach wall SW from the cardia CA to the pylorus PY into a tubular shape.

First, the insertion step (S11) of inserting the overtube OT provided with the tubular body 11 and the stomach wall support 12 in a state in which the stomach wall support 12 is housed inside of the tubular body 11, into the vicinity of the cardia CA of the stomach S via the mouth of the patient is performed.

Next, the distending step (S12) is performed by pulling the operation wire 15A with an operation of the transfer mechanism 15. At this time, the stomach wall support 12 moves until the inner lateral face 12b comes into a contact with the window 16 of the tubular body 11 so as to expose the window 16 of the stomach wall support 12 from the inside of the tubular body 11 to the outside thereof.

Then the suturing step (S13) is performed by aspirating the stomach S by the aspirator not illustrated, and the stomach S is contracted. Upon contraction of the stomach S, the stomach wall SW attaches to the stomach wall support 12.

By reducing the internal pressure of the stomach wall support 12 compared to a pressure of the stomach S, a part of the stomach wall SW is pulled into the windows 16 so as to aspirate the stomach wall SW, resulting a formation of a tubular section having a diameter larger than the inner diameter of the cardia CA within the stomach S by the stomach wall support 12.

Here, by pulling the operation wire 15A at the operation section with a high-frequency power being supplied from a high-frequency power source (not illustrated), the high-frequency electrodes 17 moves to the tubular body 11 side by crossing through the window 16 by incising or cauterizing a mucous of the stomach wall SW, thereby promoting coalescence after the suturing treatment.

The stomach wall SW is then sutured by suturing needles 18B with a rotation of the axis 18A by an operation on an operation knob.

Upon completion of suturing, the transfer mechanism 15 is operated again and the stomach wall support 12 is pulled into the tubular body 11 by pulling the operation wire 15A so that the outer lateral face 12a is returned to the same plane as the lateral face of the tubular body 11. Then the entire suturing tool 10 is drawn out from the mouth of the patient.

According to the suturing tool 10 and the suturing methods using the same, the same effect and action can be obtained as described in the first embodiment.

Third Embodiment

Next, a third embodiment will be described in line with FIGS. 14 to 17.

The third embodiment differs from the second embodiment in that a stomach wall support 21 of a suturing tool 20 according to the present embodiment is pivotally mounted on a pivot support pin 25 as a part of a lateral face of a tubular body 22 so as to be detachably mounted to a window 23 formed on a tubular body 22.

Both of the axis 18A and the suturing needles 18B are housed inside of the tubular body 22 in a position where the suturing needles 18B can pierce the stomach wall SW aspirated from a window 23.

The window 23 is formed in a substantially rectangular shape in plan view along the central axis C as the longitudinal direction.

The stomach wall support 21 is also formed in a substantially rectangular shape in plan view along the central axis C as the longitudinal direction so as to cover the window 23. A distal end 21a of the stomach wall support 21 is pivotally mounted about the pivot support pin 25 which elongates to a direction crossing with the central axis C so as to freely rotate about the pivot support pin 25.

The stomach wall support 21 is formed in the same curved-shape as the lateral face of the tubular body 22 and is provided with an outer lateral face 21b on the outer peripheral side and an inner lateral face 21c on the inner peripheral side of the stomach wall support 21. The stomach wall support 21 is rotated by a transfer mechanism not illustrated.

Next, the action of the suturing tool 20 according to the present embodiment is described along with the suturing method.

The suturing procedure according to the present embodiment includes an insertion step (S21) of inserting the overtube OT provided with the stomach wall support 21 into the stomach S via the mouth of the patient; a distending step (S22) in which the tubular body 22 is projected out within the stomach S; and a suturing step (S23) of suturing a stomach wall SW from the cardia CA to the pylorus PY of the stomach S into a tubular shape.

First, the insertion step (S21) of inserting the stomach wall support 21 in a state in which the stomach wall support 21 is closed so as to cover the window 23 of the tubular body 22, into the vicinity of the cardia CA of the stomach S via the mouth of the patient is performed.

Next, the distending step (S22) is performed by pivoting the stomach wall support 21 about the pivot support pin 25, so that a proximal end 21d of the stomach wall support 21 moves away from the tubular body 22, and the window 23 of the stomach wall support 21 is exposed.

Figure 16:
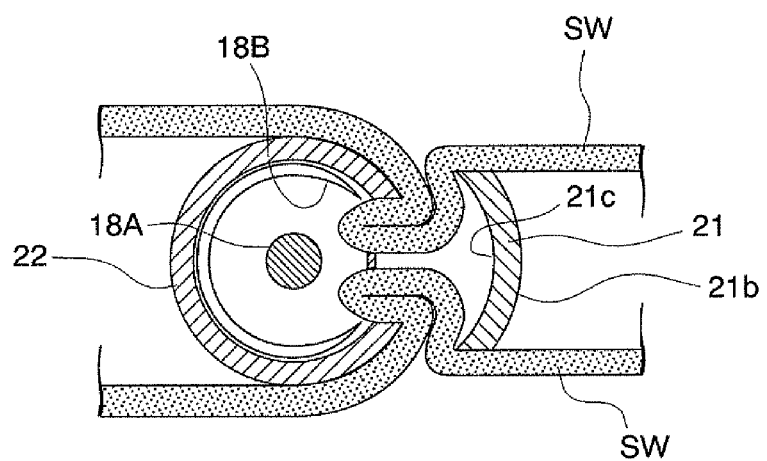
FIG. 16 is a diagram showing a state of clipping the stomach wall in the suturing procedure according to the third embodiment.

Then the suturing step (S23) is performed by aspirating the stomach S by the aspirator (not illustrated), and the stomach S is contracted. Upon contraction of the stomach S, the stomach wall SW attaches to both sides of the stomach wall support 21 (i.e., the outer lateral face 21b and the inner lateral face 21c as shown in FIG. 16), resulting in the formation of a tubular section having a diameter larger than the inner diameter of the cardia CA within the stomach S by the tubular body 22.

Then a portion of the stomach wall SW surrounded by the window 23 is sutured with the suturing needles 18B by rotating the axis 18A.

According to the suturing tool 20 and a suturing method using the same, the same action and effect as those of the second embodiment can be obtained.

Figure 17:
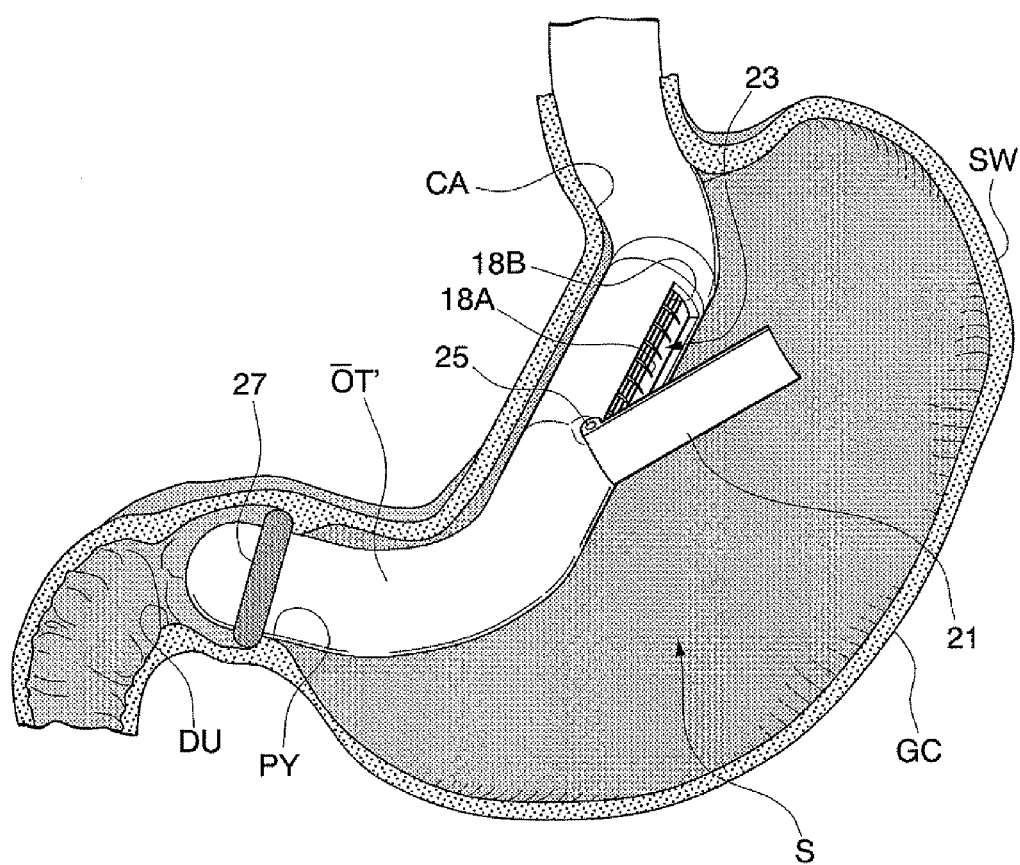
FIG. 17 is a diagram showing a modified suturing procedure according to the third embodiment.

The tubular body 22 may be disposed on any position along the overtube OT' as shown in FIG. 17, and is not limited to being disposed on the distal end of the tubular body 22. The window 23 of a tubular body 26 is disposed in the vicinity of the cardia CA, and the distal end of the tubular body 26 is disposed in the duodenum DU by passing through the pylorus PY.

At this time, it is preferable to provide a balloon 27 which expands its diameter so as to close the duodenum DU.

By providing the balloon, the duodenum DU can be closed by inflating the balloon and the position of the tubular body 22 can be determined with respect to the stomach S thereby a precise suturing treatment can be ensured.

Fourth Embodiment

Figure 18:
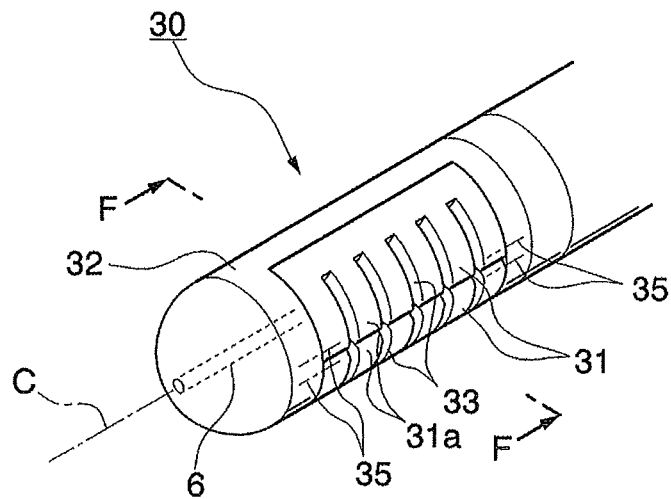
FIG. 18 is a diagram showing the principal portions of a suturing tool according to a fourth embodiment.
Figure 19:
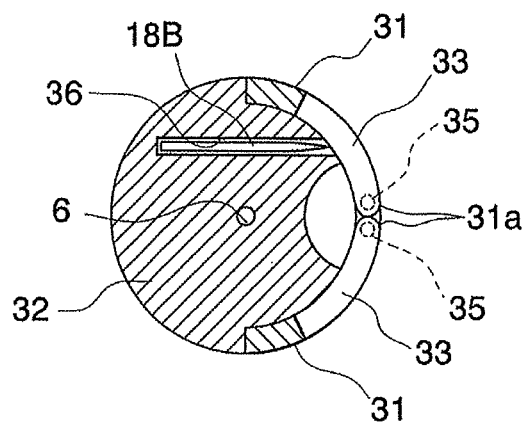
FIG. 19 is a cross-sectional view as seen from the line F-F in FIG. 18.

Next, a fourth embodiment will be described in line with FIGS. 18 to 20.

The fourth embodiment differs from the third embodiment in that a stomach wall support 31 of a suturing tool 30 according to the present embodiment is pivotally mounted on a lateral face of a tubular body 32 about a pivot support pin 35 so as to engage with a window 33 formed on the tubular body 32, and is provided as a part of the lateral face of the tubular body 32.

The stomach wall support 31 is part of the tubular body formed along a periphery thereof and is divided at the center along the periphery of the stomach wall support 31 hence the stomach wall support 31 is provided as a pair. An opposed end 31a of each pair of the stomach wall support 31 is pivotally mounted so as to freely rotate about the pivot support pin 35 on the lateral face of the tubular body 32.

The stomach wall support 31 is formed in the same curved-shape as the lateral face of the tubular body 32. The stomach wall support 31 is rotated by a transfer mechanism (not illustrated).

The window 33 provided on the lateral face of the tubular body 32 is formed in a strip-shape so that the pair of the stomach wall supports 31 engage each other. The suture needles 1 SB are provided in the vicinity of the window 33.

The suture needles 18B are formed of a super-elastic wire and curved in advance, and is housed in a tubular shaped receiver 36 included in a tubular body 32 by being stretched into a straight shape at the time of operation.

Next, action of a suturing tool 30 according to the present embodiment is described along with the suturing method.

Similar to the third embodiment, the suturing procedure according to the present embodiment consists of an insertion step (S21) of inserting the overtube OT provided with the stomach wall support 31 into the stomach S via the mouth of the patient; a distending step (S22) in which the stomach wall support 31 is projected out within the stomach S; and a suturing step (S23) of suturing the stomach wall SW into a tubular shape from the cardia CA to the pylorus PY.

First, the insertion step (S21) of inserting the overtube OT provided with the stomach wall support 31 into the mouth of the patient is performed.

Next, the distending step (S22) is performed by pivoting the pair of the stomach wall supports 31 about the pivot support pin 35 with an operation of a transfer mechanism, so that another end of the pair of stomach wall supports 31 move away from the tubular body 32. With this movement, the window 33 formed on the stomach wall support 31 also moves away from the tubular body 32.

In the suturing step (S23), the stomach S is aspirated by the aspiration lumen 6 operated by an aspirator (not illustrated), and the stomach S is contracted.

Figure 20:
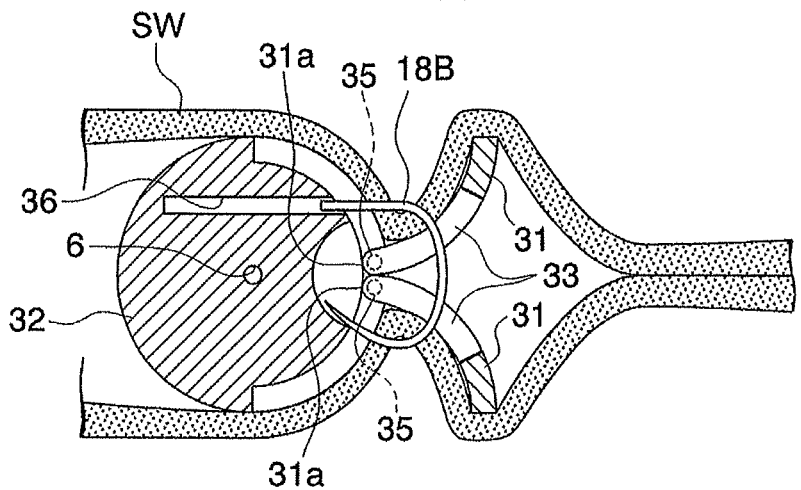
FIG. 20 is a diagram showing a state of clipping the stomach wall in the suturing procedure according to the fourth embodiment.

Upon contraction of the stomach S, the stomach wall SW attaches onto an inner side of the stomach wall support 31 as shown in FIG. 20, resulting a formation of a tubular section having its diameter larger than the inner diameter of the cardia CA, within the stomach S by the stomach wall support 31.

Then a portion of the stomach wall SW surrounded by the window 33 is sutured with the suturing needles 18B by rotating the axis.

According to the suturing tool 30 and a suturing method using the same, the same action and effect of those in the third embodiment can be obtained.

Fifth Embodiment

Next, a fifth embodiment will be described in line with FIGS. 21 to 27.

Figure 21:
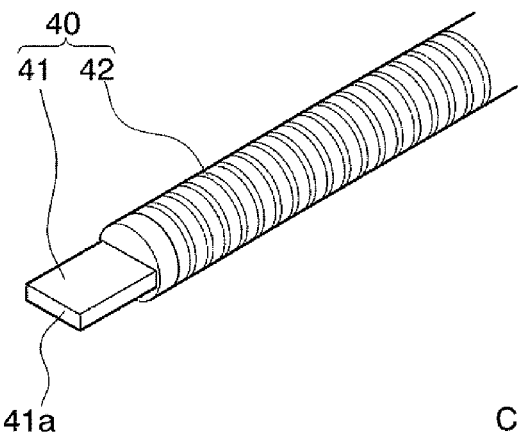
FIG. 21 is a diagram showing the principal portions of a high-frequency treatment tool according to a fifth embodiment.

The fifth embodiment differs from the first embodiment in that a high-frequency treatment tool 40 in the present embodiment is used in the suturing procedure within the stomach S or within the abdominal cavities with the suturing tools described in the above embodiments as shown in FIG. 21, and is provided with a high-frequency electrode 41 inserted into an instrument channel of an endoscope E in a manner of freely protrudes and retracts.

The high-frequency electrode 41 is connected to a high-frequency power source not illustrated via a flexible elongated shaft of a conductive portion 42. A distal end face 41a of the high-frequency electrode 41 is formed in a substantially rectangular shape in plan view in which its longitudinal direction thereof has a substantially same length of an internal diameter of an insertion channel CH of the treatment tool.

Figure 22:
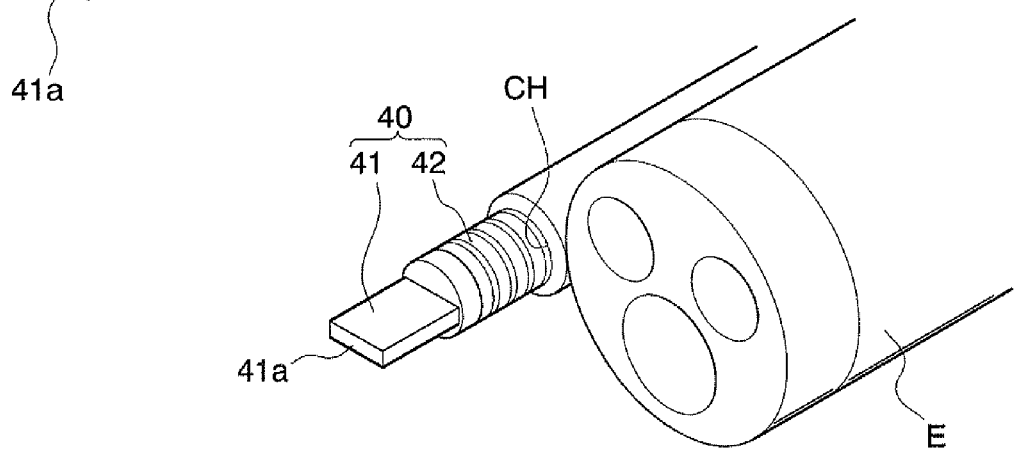
FIG. 22 is a diagram showing a state of the high-frequency treatment tool when in use according to the fifth embodiment.
Figure 23:
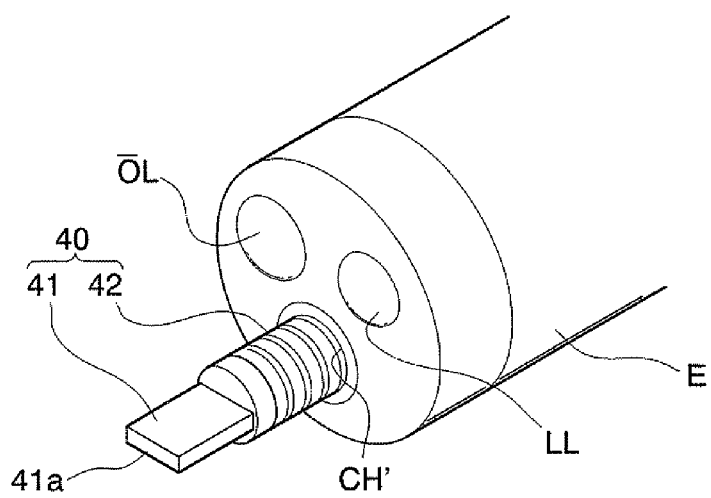
FIG. 23 is a diagram showing a modified state of the high-frequency treatment tool when in use according to the fifth embodiment.

The insertion channel of the treatment tool CH is disposed on an outer periphery of the endoscope E as shown in FIG. 22. Alternatively, the high-frequency treatment tool 40 may also be inserted into a pre-formed insertion channel CH' of the endoscope E, as shown in FIG. 23.

Next, the action of the high-frequency treatment tool 40 according to the present embodiment is described along with the suturing method.

The high-frequency treatment tool 40 according to the present embodiment is used for cauterizing sutured tissues after completion of the insertion step (SOI), the distending step (S02) and the suturing step (S03) in the first embodiment.

After completion of the treatment described in the first embodiment, the high-frequency electrode 41 inserted into the insertion channel CH is made to protrude from the distal end thereof.

Figure 24:
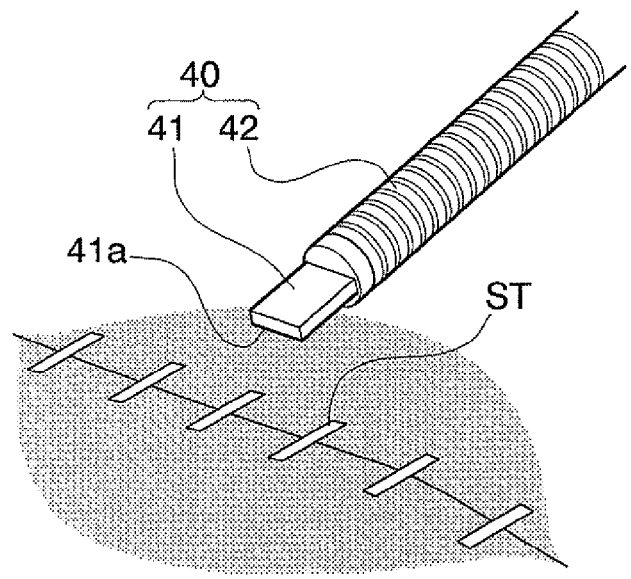
FIG. 24 is a diagram showing a state of the high-frequency treatment tool when it is used in the suturing procedure according to the fifth embodiment.
Figure 25:
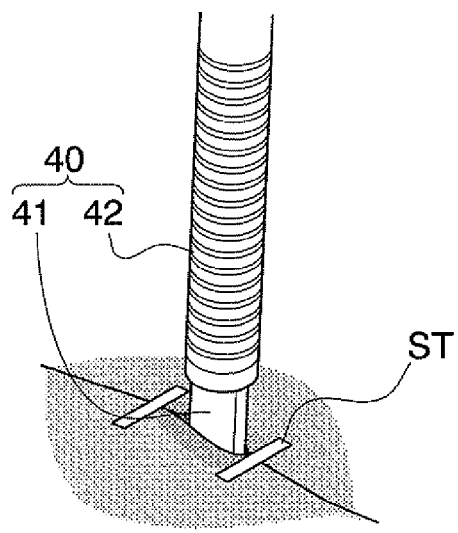
FIG. 25 is a diagram showing a state of the high-frequency treatment tool when it is used in the suturing procedure according to the fifth embodiment.
Figure 26:
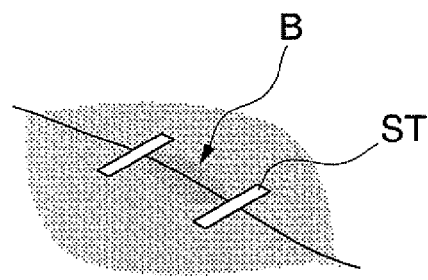
FIG. 26 is a diagram showing a state of the high-frequency treatment tool when it is used in the suturing procedure according to the fifth embodiment.

As shown in FIG. 24, a longitudinal direction of a substantially rectangular shape in plan view of the distal end face 41a of the high-frequency electrode 41 is set to align between stitches ST, and the distal end face 41a abuts a tissue as shown in FIG. 25. Then a cauterized section B is formed by cauterizing the section of tissue abutted with the high-frequency electrode 41 as shown in FIG. 26, by a high-frequency current of predetermined condition being supplied from a high-frequency power source.

According to the high-frequency treatment tool 40, sutured tissue can be cauterized, thereby promoting coalescence of the tissues after the suturing treatment.

Figure 27:
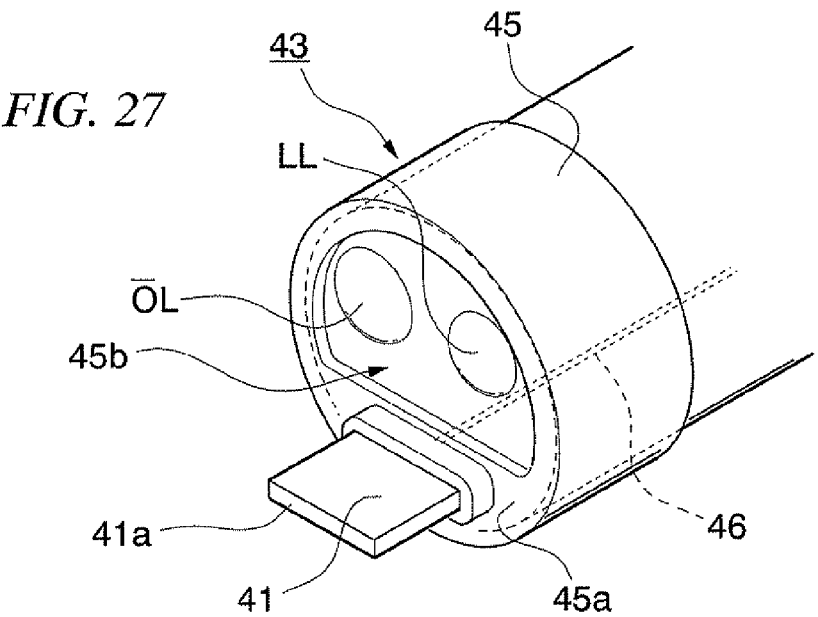
FIG. 27 is a diagram showing the principal portions of another modification example of the high-frequency treatment tool according to the fifth embodiment.

Alternatively, as shown in FIG. 27, a high-frequency treatment tool 43 may be provided with a cap 45 detachably disposed at a distal end of the endoscope E, and the high-frequency electrode 41 may be disposed in a protruded manner from the distal end face of the cap 45 so that an opening portion 45b may be disposed on a distal end face 45a adjacent to the high-frequency electrode 41.

In this case, even if the cap 45 is disposed at the distal end of the endoscope E, the opening portion 45b still opens having a sufficient size to expose an object lens OL and a lamination lens LL via the opening portion 45b. A distal end of a conductive wire 46 for supplying electricity to the high-frequency electrode 41 disposed along the endoscope E is connected to the cap 45.

According to the high-frequency treatment tool 43, by disposing the cap 45 at the distal end of the endoscope E, the high-frequency electrode 41 can be advanced into a sutured portion along with the endoscope E, thereby the tissue can be cauterized.

Sixth Embodiment

Figure 28:
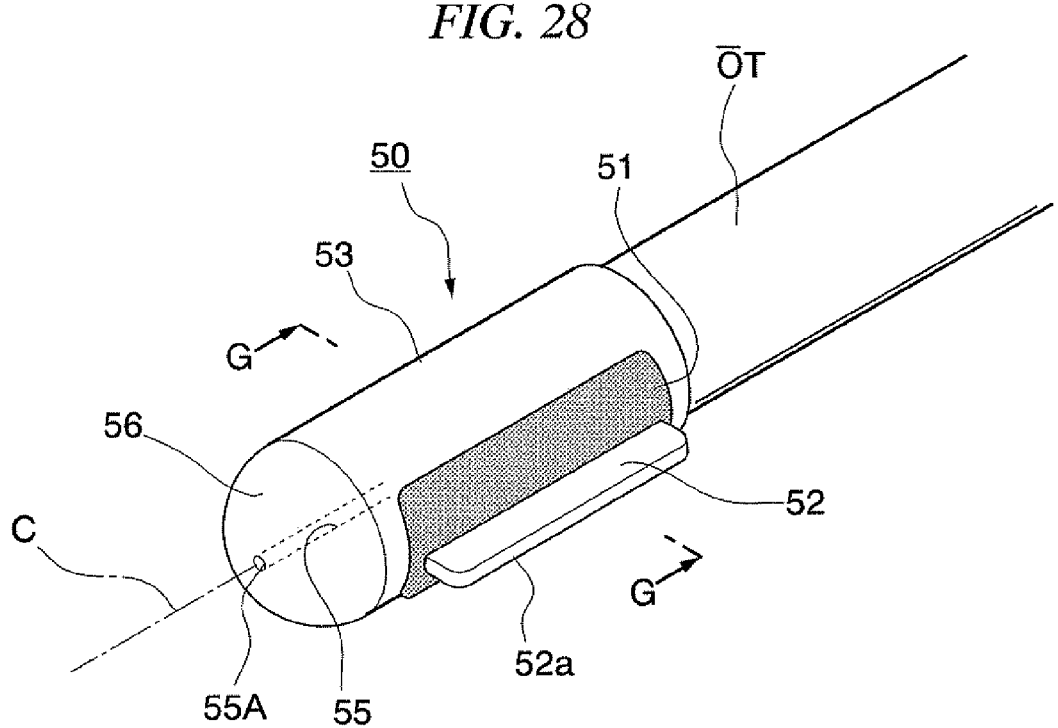
FIG. 28 is a diagram showing the principal portions of a high-frequency treatment tool according to a sixth embodiment.
Figure 29:
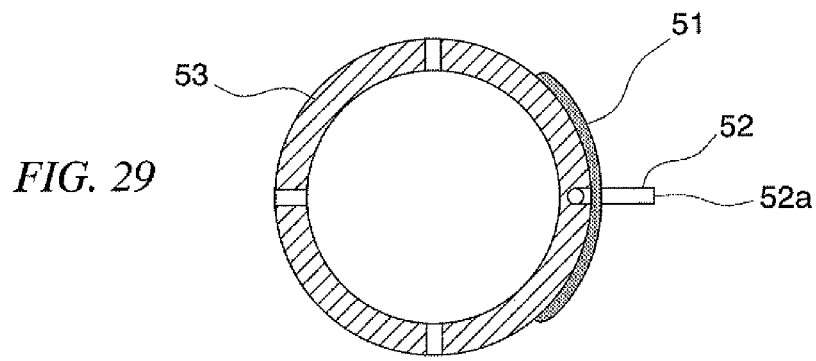
FIG. 29 is a cross-sectional view as seen from the line G-G in FIG. 28.

A sixth embodiment differs from the fifth embodiment in that a provision of a balloon 51 which inflates by fluid being introducing thereinto and a high-frequency electrode 52 disposed on an outer peripheral surface of an inflatable balloon 51 in a high-frequency treatment tool 50 according to the present embodiment, as shown in FIGS. 28 and 29.

A cap 53 forms in a cylindrical-shape and a distal end portion 56 including an opening 55A of an aspiration lumen 55 in the center thereof is disposed on a distal end of the cap 53.

The balloon 51 is disposed on a lateral surface of the cap 53 and inflates by fluid being flowed thereinto via a connecting tube (not illustrated). A high-frequency electrode 52 is disposed on an outer surface of the balloon 51 in a way that the longitudinal direction of a distal end face 52a aligns with the central axis C of the cap 53.

Next, action of the high-frequency treatment tool 50 according to the present embodiment is described along with the suturing method.

The high-frequency treatment tool 50 according to the present embodiment is used for cauterizing sutured tissues in an insertion step (S33) and a distending step (S32) instead of the insertion step (S01) and the distending step (S02) as a pre-treatment of the suturing step (S03) in the first embodiment.

In the insertion step (S31), the cap 53 is fitted on the distal end of the overtube OT instead of an endoscope, and a high-frequency treatment tool 50 along with the overtube OT is inserted into the vicinity of the cardia CA of the stomach S via the mouth of the patient. At this time, the balloon 51 is deflated.

In the distending step (S32), a fluid is introduced into the balloon 51 via the connecting tube. By introducing fluid into the balloon 51, the balloon 51 is inflated so that the high-frequency electrode 52 moves away from the cap 53; in other words, moving toward the outer diameter.

In this state, the stomach S is aspirated by an aspiration lumen 55 with an operation of an aspirator (not illustrated), and the stomach S is contracted. Upon contraction of the stomach S, the stomach wall SW attaches to the outer peripheral surface of the balloon 51 and to the high-frequency electrode 52. Then, a high-frequency electricity is supplied to the high-frequency electrode 52.

Figure 30:
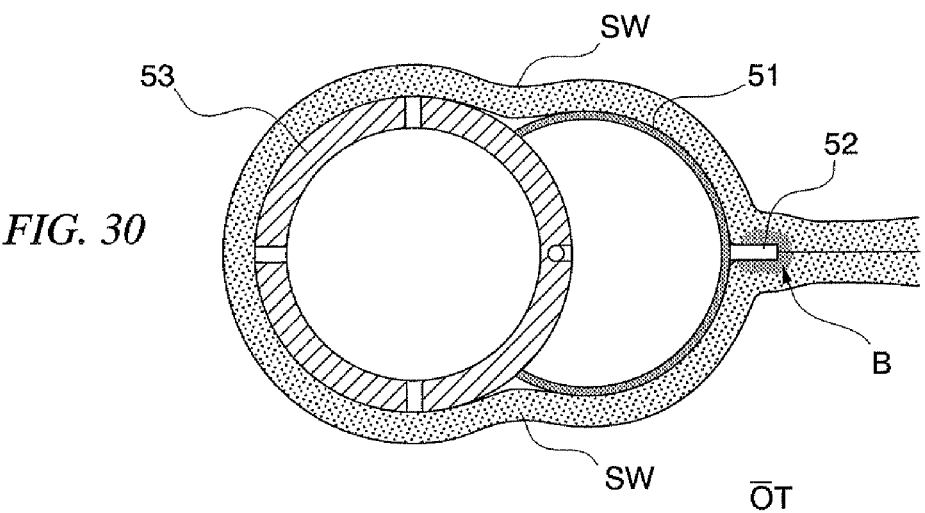
FIG. 30 is a view describing a state of the high-frequency treatment tool when it is used in the suturing procedure according to the sixth embodiment.

At this time, as shown in FIG. 30, a cauterized section B is formed by a tissue which is in contact to the high-frequency electrode 52.

At this state, the cap 53 is advanced from a position in the vicinity of the cardia CA to the pylorus PY of the stomach S by advancing the overtube OT. Thus, a tubular section in which the diameter is larger than the inner diameter of the cardia CA is formed within the stomach S.

The high-frequency treatment tool 50 is then drawn out and an endoscope provided with a suturing tool (not illustrated) is inserted into the overtube OT instead, and the suturing step (S03) is performed by the suturing tool.

According to the high-frequency treatment tool 50, a tubular section in which the diameter is larger than the inner diameter of the cardia CA can be formed prior to the suturing step. Since the tissue is cauterized at this time, the tissue can be coalesced hence the suturing procedure can be performed in a stable manner.

Figure 31:
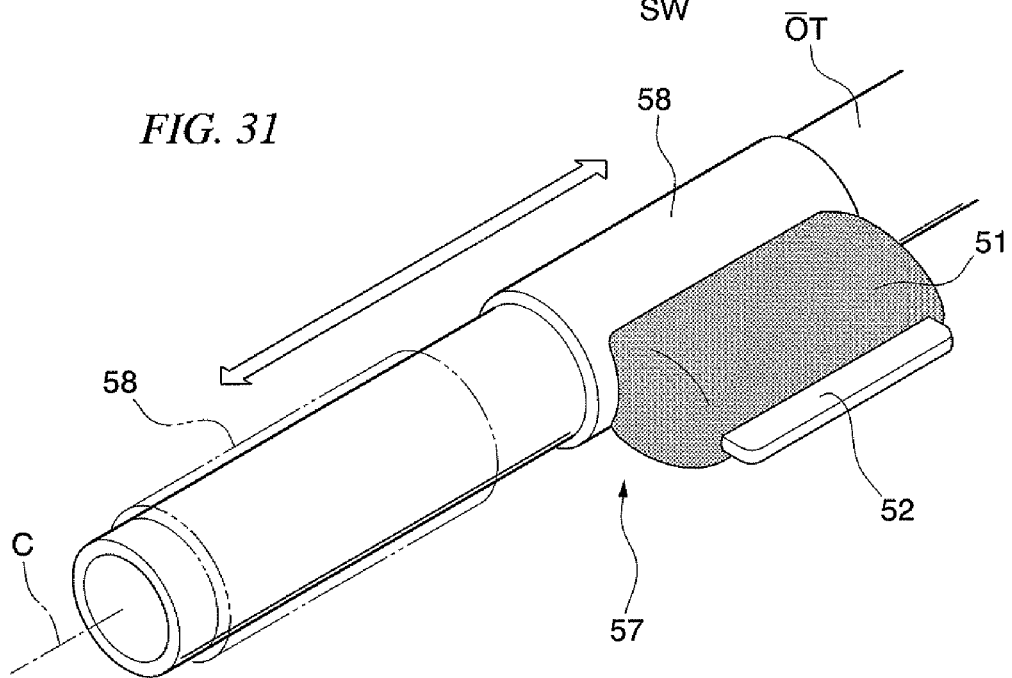
FIG. 31 is a view showing the principal portions of another modification example of the high-frequency treatment tool according to the sixth embodiment.

Alternatively, as shown in FIG. 31, a cap 58 of a high-frequency treatment tool 57 may be disposed on the overtube 58 along the central axis C so as to freely advance and retract. In such a case, it is not necessary to move the entire overtube OT to the pylorus side PY, only the cap 58 may be moved with respect to the overtube OT.

While preferred embodiments of the invention have been described and illustrated above, it should be understood that these are exemplary of the invention and are not to be considered as limiting. Additions, omissions, substitutions, and other modifications can be made without departing from the scope of the invention. Accordingly, the invention is not to be considered as being limited by the foregoing description, and is only limited by the scope of the appended claims.

For example, although the suturing tool is disposed at the distal end of the endoscope E in the above embodiment, the present invention is not limited thereto; for example, it may be disposed at the distal end of the overtube OT.

What is claimed is:

1. An endoscopic treatment tool being capable of being inserted into one of a hollow organ and an abdominal cavity through a natural orifice and being capable of performing a suturing treatment within one of the hollow organ and the abdominal cavity, the endoscopic treatment tool comprising:
   a tubular body formed in a tubular shape that has a diameter which is smaller than a smallest diameter of a passage from the natural orifice to one of the hollow organ and the abdominal cavity, and the tubular body provided with an opening portion at a lateral face of the tubular body;
   a pivot support provided along the lateral face of the tubular body, positioned parallel to a center axis line of the tubular body and across the opening portion;
   a hollow organ lining support consisting of a pair of members which are configured such that a first end part of each of the pair of members is pivotally supported by the pivot support and a second end part of each of the pair of members is extended from a lateral side of the pivot support toward an open end of the opening portion, the hollow organ lining support forming a part of the lateral face of the tubular body when the second end parts of the pair of members are positioned at the open end of the opening portion, and the pair of members provided to be capable of pivoting about the pivot support such that the second end parts move away from the tubular body,
   a suture needle provided in the tubular body; and
   an aspiration section provided in the tubular body, wherein the pair of members of the hollow organ lining support are provided with a slit through which the suture needle is capable of passing,
   wherein when the opening portion is opened by pivoting each of the pair of members such that the second end part of each member moves away from the tubular body, a distal end of the suture needle is capable of protruding from an inside of the tubular body via the opening portion, moving through-the slit of the pair of the members, and then inserting into the opening portion from an outer side of the tubular body, and
   wherein the suture needle is configured to be capable of suturing one of the hollow organ and the abdominal wall when one of the hollow organ and the abdominal cavity is attached to both of the opening portion and an inner wall side of the pair of members by aspirating the one of the hollow organ and the abdominal wall by the aspiration section.

2. The endoscopic treatment tool according to claim 1, wherein:
   the hollow organ lining support is mounted on the tubular body so as to be capable of fitting into the opening portion when the second end parts of the pair of members are positioned at the open end of the opening portion.

3. The endoscopic treatment tool according to claim 1, wherein the slit comprises a plurality of slits and the suture needle comprises a plurality of suture needles.

* * * * *